(12) United States Patent
Poursohi et al.

(10) Patent No.: US 9,437,097 B2
(45) Date of Patent: **\*Sep. 6, 2016**

(54) SYSTEMS AND METHODS FOR USING ROBOTS TO MONITOR ENVIRONMENTAL CONDITIONS IN AN ENVIRONMENT

(71) Applicant: Google Inc., Mountain View, CA (US)

(72) Inventors: Arshan Poursohi, Berkeley, CA (US); Ryan Hickman, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/455,896

(22) Filed: Aug. 9, 2014

(65) Prior Publication Data
US 2014/0347182 A1    Nov. 27, 2014

Related U.S. Application Data

(63) Continuation of application No. 13/758,055, filed on Feb. 4, 2013, now Pat. No. 8,830,057.

(60) Provisional application No. 61/596,780, filed on Feb. 9, 2012.

(51) Int. Cl.
*G08B 21/00*  (2006.01)
*G08B 21/18*  (2006.01)
(Continued)

(52) U.S. Cl.
CPC ............. *G08B 21/182* (2013.01); *B25J 9/161* (2013.01); *B25J 9/1671* (2013.01); *G01N 33/00* (2013.01); *G05B 15/02* (2013.01); *G06N 3/008* (2013.01); *G05B 2219/2642* (2013.01); *G05B 2219/39168* (2013.01); *G08B 13/00* (2013.01); *G08B 17/00* (2013.01); *G08B 21/12* (2013.01)

(58) Field of Classification Search
CPC ....... G06N 3/008; B25J 9/161; B25J 9/1671; A47F 10/00; G08B 25/009; G05B 2219/39168
USPC .................... 340/540, 539.26; 700/245, 246; 318/568.12; 901/46
See application file for complete search history.

(56) References Cited

U.S. PATENT DOCUMENTS 5,446,445 A    8/1995  Bloomfield et al.
6,507,773 B2 *  1/2003  Parker ................... G06N 3/008
                                                318/568.11
(Continued)

OTHER PUBLICATIONS

Valin, Jean-Marc et al., Robust Localization and Tracking of Simultaneous Moving Sound Sources Using Beamforming and Particle Filtering, Robotics and Autonomous Systems, vol. 55, Issue 3, pp. 216-228, Mar. 31, 2007.

*Primary Examiner* — John A Tweel, Jr.
(74) *Attorney, Agent, or Firm* — McDonnell Boehnen Hulbert & Berghoff LLP

(57) ABSTRACT

Methods and devices are disclosed for monitoring environmental conditions in one or more environments. In one embodiment, the method includes maintaining a plurality of environmental-condition thresholds, each of which corresponds to an environmental condition and is predetermined based on data corresponding to the environmental condition that is received from a plurality of robots. The method further includes receiving from a first robot first data corresponding to a first environmental condition in a first environment. The method may still further include making a first comparison of the first data and a first environmental-condition threshold corresponding to the first environmental condition and, based on the first comparison, triggering a notification. Triggering the notification may comprise transmitting to the robot instructions to transmit the notification to at least one of a call center and a remote device.

20 Claims, 7 Drawing Sheets

(51) Int. Cl.
  *B25J 9/16*   (2006.01)
  *G06N 3/00*   (2006.01)
  *G01N 33/00*  (2006.01)
  *G05B 15/02*  (2006.01)
  *G08B 13/00*  (2006.01)
  *G08B 17/00*  (2006.01)
  *G08B 21/12*  (2006.01)

(56) References Cited

U.S. PATENT DOCUMENTS

| | | | |
|---|---|---|---|
| 6,584,375 B2 * | 6/2003 | Bancroft | A47F 10/00 |
| | | | 235/383 |
| 6,763,282 B2 | 7/2004 | Glenn et al. | |
| 7,030,757 B2 | 4/2006 | Matsuhira et al. | |
| 7,082,351 B2 * | 7/2006 | Hara | G05D 1/104 |
| | | | 318/568.16 |
| 7,349,758 B2 | 3/2008 | Miro et al. | |
| 8,111,156 B2 * | 2/2012 | Song | G08B 13/19647 |
| | | | 340/539.22 |
| 8,307,061 B1 | 11/2012 | Hickman et al. | |
| 8,386,078 B1 | 2/2013 | Hickman et al. | |
| 8,830,057 B1 * | 9/2014 | Poursohi | G08B 21/182 |
| | | | 340/540 |
| 9,069,356 B2 * | 6/2015 | Papaefstathiou | G05D 1/0038 |
| 2006/0154642 A1 | 7/2006 | Scannell, Jr. | |
| 2007/0011683 A1 | 1/2007 | Helander | |
| 2009/0303042 A1 | 12/2009 | Song et al. | |

* cited by examiner

SYSTEMS AND METHODS FOR USING ROBOTS TO MONITOR ENVIRONMENTAL CONDITIONS IN AN ENVIRONMENT

CROSS-REFERENCE TO RELATED APPLICATIONS

This application is a continuation of U.S. patent application Ser. No. 13/758,055 filed on Feb. 4, 2013, the contents of which are hereby incorporated by reference.

This application claims the benefit of U.S. Provisional Application No. 61/596,780 filed on Feb. 9, 2012, the entirety of which is herein incorporated by reference.

BACKGROUND

Various sensors may be used in an environment to sense one or more environmental conditions of the environment. As a first example, many homes include a smoke sensor that senses a level of smoke in the home. As a second example, many warehouses include a temperature sensor that senses an ambient temperature in the warehouse. Other sensors are used as well.

Some sensors may be equipped with an alarm, such as a visual or audible alarm, that may be triggered based on the sensed environmental conditions. Using the first example above, a smoke alarm in a home may trigger an audible alarm when a sensed level of smoke in the home exceeds an acceptable level. Other sensors may be equipped to transmit a notification, such as a textual notification, to another entity based on the sensed environmental conditions. Using the second example above, a temperature sensor in a warehouse may transmit a notification to a control center or other entity when a sensed ambient temperature is outside an acceptable range of ambient temperatures.

SUMMARY

Disclosed herein are cloud-based systems and methods for using robots to monitor environmental conditions in one or more environments. The disclosed cloud-based system may include a server and one or more robots in environments. Each of the one or more robots may include a server and one or more robots in environments.

Each robot may collect data regarding one or more environmental conditions in its environment and transmit the collected data to the server. The server may use the data received from the robots to maintain a number of environmental-condition thresholds. Further, the server may use the environmental-condition thresholds to evaluate the environmental condition(s) in the robots' environments.

In one aspect, a method for monitoring an environmental condition in an environment is disclosed. The method includes maintaining a plurality of environmental-condition thresholds, each of which corresponds to an environmental condition and is predetermined based on data corresponding to the environmental condition that is received from a plurality of robots. The method further includes receiving from a first robot first data corresponding to a first environmental condition in a first environment. The method still further includes making a first comparison of the first data and a first environmental-condition threshold corresponding to the first environmental condition and, based on the first comparison, triggering a notification.

In another aspect, a nontransitory computer readable medium is disclosed having stored therein instructions executable by a computing device to cause the computing device to perform the functions of the method described above.

In yet another aspect, a robot for monitoring environmental conditions in environments is disclosed. The robot includes at least one of on-board sensors and a remote sensor interface coupled to at least one remote sensor. The on-board sensors and the remote sensor interface are configured to collect first data corresponding to a first environmental condition. The robot further includes a server interface configured to transmit to a server a request for a first environmental-condition threshold corresponding to the first environmental condition and to receive from the server an indication of the first environmental-condition threshold, wherein the first environmental-condition threshold is predetermined based on data corresponding to the first environmental condition that is received from a plurality of robots. The robot further includes at least one processor; and data storage comprising instructions executable by the at least one processor to make a comparison of the first data and the first environmental-condition threshold and, based on the comparison, transmit a notification.

In still another aspect, a server for operating in a system for monitoring environmental conditions in environments is disclosed. The server includes a first input interface configured to receive from a first robot first data corresponding to a first environmental condition in a first environment, at least one processor, and data storage. The data storage comprises a plurality of environmental-condition thresholds, each of which corresponds to an environmental condition and is predetermined based on data corresponding to the environmental condition and received from a plurality of robots. The data storage further comprises instructions executable by the at least one processor to make a first comparison of the first data and a first environmental-condition threshold corresponding to the first environmental condition and, based on the first comparison, trigger a notification.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

In the Figures.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

This disclosure may disclose, inter alia, methods and systems for robot-cloud computing. In particular, in examples described herein, a number of robots and/or other client devices may interact with a cloud server to share data corresponding to one or more environmental conditions in a number of environments. The cloud server may, in turn, use the data from the robots and/or other client devices to determine a threshold for each environmental condition. These thresholds may be referred to as environmental-condition thresholds.

Thereafter, a robot may collect data corresponding to an environmental condition in the robot's environment. The robot may transmit the data to the cloud server, and the cloud server may compare the data from the robot with an environmental-condition threshold for the environmental condition. Alternately or additionally, the robot may transmit to the cloud server a request for the environmental-condition threshold for the environmental condition, the robot may receive the environmental-condition threshold, and the robot may compare the data from the robot with the environmental-condition threshold. In either case, based on the comparison, the cloud server or robot may determine whether the environmental condition in the robot's environment is at an acceptable level or an unacceptable level. When the environmental condition is at an unacceptable level, the cloud server or robot may trigger a notification.

Figure 1:
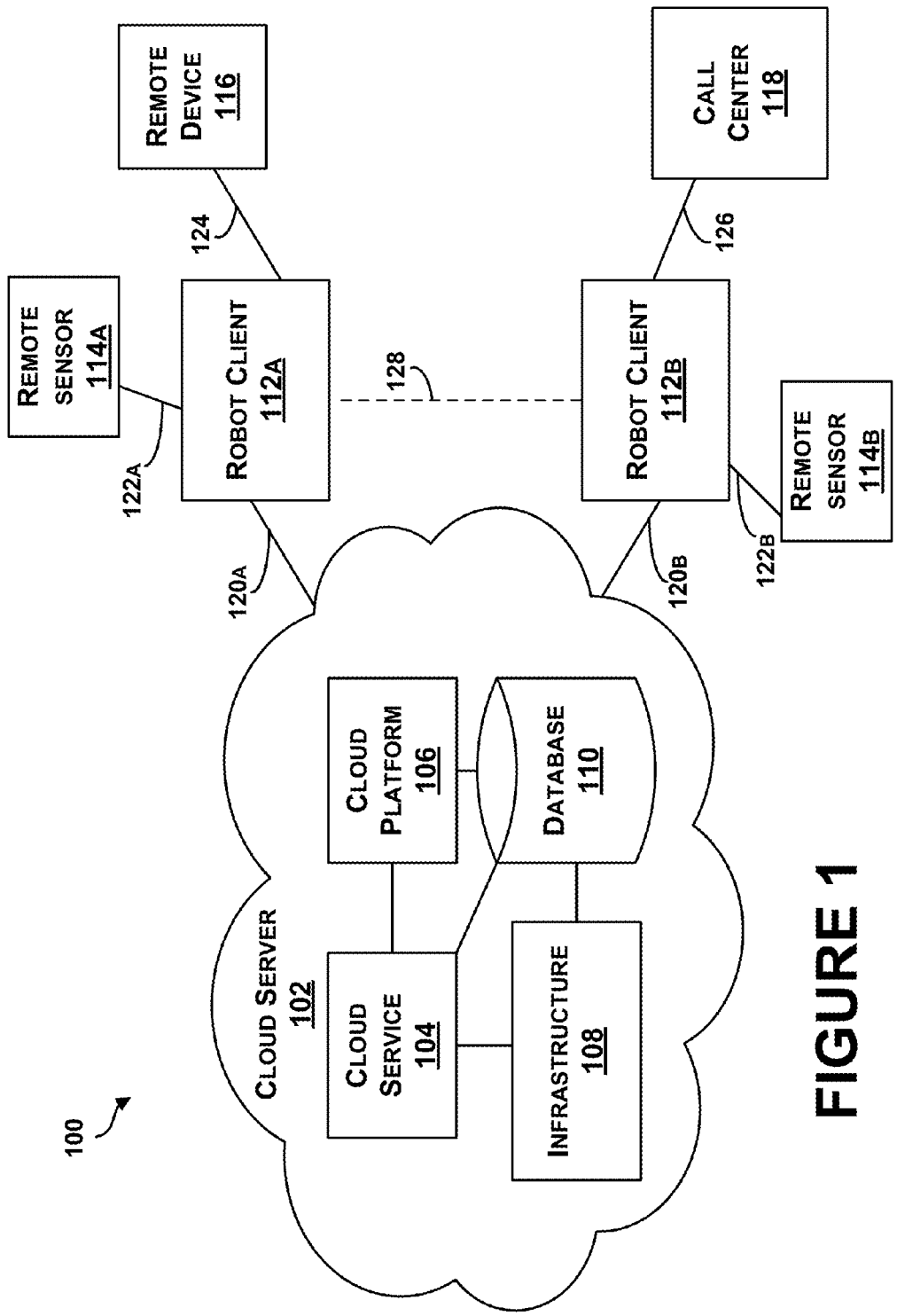
FIG. 1 is an example a system for monitoring environmental conditions in environment.

Referring now to the figures, FIG. 1 is an example a system 100 for monitoring environmental conditions in an environment. As shown in FIG. 1, the system 100 includes a cloud server 102 coupled to two robot clients 112A and 112B via communication links 120A and 120B, respectively.

While one cloud server 102 and two robot clients 112A and 112B are shown, more or fewer cloud servers and robot clients are possible as well. In addition, different types of client devices, besides robot clients 112A and 112B, may be coupled to the cloud server 102. For example, any device that may generally comprise a display system, memory, and a processor may be coupled to the cloud server 102.

The system 100 may be configured to operate in a cloud-based computing architecture. Cloud-based computing generally refers to networked computer architectures in which application execution and storage may be divided, to some extent, between server and client devices. In the system 100, the cloud server 102 may be said to be a server device, while the robot clients 112A and 112B may be said to be client devices. Thus, in the system 100, application execution and storage may be divided, to some extent, between the cloud server 102 and the robot clients 112A and 112B. In particular, in the system 100, environmental-condition thresholds data and instructions executable to determine the environmental-condition thresholds, to compare received data with the environmental-condition thresholds, and to trigger notifications may be divided, to some extent, between the cloud server 102 and the robot clients 112A and 112B.

In some embodiments, the cloud server 102 may store copies of the environmental-condition thresholds data and/or the instructions. At least some of this data (e.g., data corresponding to an environmental-condition threshold) and instructions (e.g., instructions to trigger notifications) may be dynamically delivered to and/or downloaded by the robot clients 112A and 112B, as needed or otherwise, for execution at the robot clients 112A and 112B. In this manner, the robot clients 112A and 112B may access at least some of this data and instructions on a near real-time basis.

In some embodiments, downloaded data and instructions can be tailored to the specific capabilities of the robot clients 112A and 112B accessing the cloud server 102. Further, in some embodiments, details of the architecture may be transparent to users of the robot clients 112A and 112B.

Dividing application execution and storage between the cloud server 102 and the robot clients 112A and 112B may allow more processing to be performed by the cloud server 102, taking advantage of the comparatively greater processing power and capability of the cloud server 102, for example.

In the system 100, the cloud server 102 includes a cloud service 104, a cloud platform 106, a cloud infrastructure 108, and a database 110. The cloud server 102 may include more or fewer components, and each of the cloud service 104, the cloud platform 106, the cloud infrastructure 108, and the database 110 may comprise multiple elements as well. Thus, one or more of the described functions of the system 100 may be divided up into additional functional or physical components, or combined into fewer functional or physical components. In some further examples, additional functional and/or physical components may be added to the examples illustrated by FIG. 1. Delivery of cloud computing may involve multiple cloud components communicating with each other over application programming interfaces, such as web services and three-tier architectures, for example.

The cloud server 102 may represent a networked computer architecture, and in one example, the cloud service 104 represents a queue for handling requests from client devices, such as the robot clients 112A and 112B. The cloud platform 106 may include a frontend of the cloud and may be coupled to the cloud service 104 to perform functions to interact with client devices. The cloud platform 106 may include applications used to access the cloud server 102 via a user interface, such as a web browser. The cloud infrastructure 108 may include service application of billing components of the cloud server 102, and thus, may interact with the cloud service 104. The database 110 may represent storage capabilities by the cloud server 102, and thus, may be accessed by any of the cloud service 104, the cloud platform 106, and/or the infrastructure 108. An example server is further described below in connection with FIG. 2.

As noted above, the system 100 includes robot clients 112A and 112B, each of which coupled to or otherwise configured to be capable of communicating with components of the cloud server 102.

Each of the robot clients 112A and 112B may comprise any computing device that is configured to connect to the cloud server 102 and that has an actuation capability (e.g., electromechanical capabilities). Each robot client 112A and 112B may further be a combination of computing devices. Robot client 112A may be located in a first environment and robot client 112B may be located in a second environment. The second environment may be co-located with the first environment, or may be remote from the first environment. For example, robot client 112A could be located in a first home and robot client 112B could be located in a second home, such as a home next door to the first home, or a home several miles away. Other examples are possible as well.

In some examples, one or both of robot clients 112A and 112B may collect data and upload the data to the cloud server 102. For example, one or both of robot clients 112A and 112B may collect data corresponding to one or more environmental conditions and may upload the data to the cloud server 102. In particular, robot client 112A may collect data corresponding to one or more environmental conditions in the first environment. Similarly, robot client 112B may collect data corresponding to one or more environmental conditions in the second environment. Example environmental conditions may include temperature, levels of sound, levels of light, levels of carbon monoxide, natural gas, or other gases, levels of water, motion, and parameters of one or more appliances or other devices in the environment. Other environmental conditions are possible as well.

In order to collect data corresponding to the one or more environmental conditions, robot clients 112A and 112B may include one or more on-board sensors. Example on-board sensors include gyroscopes, accelerometers, compasses, Global Positioning System (GPS) receivers, light sensors, infrared sensors, optical sensors, biosensors, radio sensors, Radio Frequency identification (RFID) systems, wireless sensors, cameras, light sensors, motion sensors, range sensors, microphones or other audio sensors, speakers, radar, capacitive sensors, touch sensors, smoke sensors, carbon monoxide sensors, natural gas sensors, gyro sensors, heat sensors, water sensors, and/or biometric sensors. Other types of on-board sensors are possible as well.

In some embodiments, in order to collect data corresponding to the one or more environmental conditions, the robot client 112A may further be coupled to a remote sensor 114A via communication link 122A, and robot client 112B may be coupled to remote sensor 114B via a communication link 122B, as shown. Remote sensors 114A and 114B may collect data corresponding to one or more environmental conditions in the first and second environments, respectively, and transmit the data to the robot clients 112A and 112B, respectively. Example remote sensors include light sensors, infrared sensors, optical sensors, biosensors, radio sensors, Radio Frequency identification (RFID) systems, wireless sensors, cameras, light sensors, motion sensors, range sensors, microphones or other audio sensors, speakers, radar, capacitive sensors, touch sensors, smoke sensors, carbon monoxide sensors, natural gas sensors, gyro sensors, heat sensors, water sensors, and/or biometric sensors. In some embodiments, the remote sensors may include or be coupled to appliances or other devices that are configured to collect data regarding their own performance. Examples of such remote sensor configurations include washing machines, dryers, refrigerators, ovens, stoves, small appliances (e.g., toasters and coffee makers), furnaces, air conditioning units, heating units, televisions, computers, fire alarms, and security systems. Other types of remote sensors are possible as well.

Thus, robot clients 112A and 112B may collect data corresponding to one or more environmental conditions in the first and second environments, respectively, through one or both of on-board sensors and remote sensors 114A and 114B.

Upon collecting the data, each of robot client 112A and robot client 112B may send the collected data to the cloud server 102 via communication links 120A and 120B, respectively. The cloud server 102 may be configured to perform calculations or analysis on the data and return processed data to the robot clients 112A and 112B. For example, the cloud server 102 may be configured to compare the received data with one or more environmental-condition thresholds and, in response to finding that some or all of the data is at an unacceptable level based on the one or more environmental-condition thresholds, return to one or both robot clients 112A and 112B instructions to trigger a notification. Alternately, upon collecting the data, each of robot client 112A and 112B may transmit to the cloud server 102 a request for the one or more environmental-condition thresholds, and, upon receiving the requested environmental-condition thresholds from the server, may compare the received data with one or more environmental-condition thresholds. In response to finding that some or all of the data is at an unacceptable level based on the one or more environmental-condition thresholds, robot clients 112A and 112B may transmit a notification. In some embodiments, prior to transmitting the notification, robot clients 112A and 112B may determine whether the data at an unacceptable level was collected at a remote sensor. When the data was collected at a remote sensor, the robot may verify the data (e.g., by moving to where the remote sensor is located and re-collecting the data, or by controlling another remote sensor to re-collect the data) before triggering the notification. An example robot client is further described below in connection with FIGS. 3A-C.

As shown in FIG. 1, robot client 112A is further connected to a remote device 116 via a communication link 124. Remote device 116 may be any type of device configured to receive the notification. For example, remote device 116 may be a laptop, mobile telephone, smartphone, personal digital assistant, tablet, or personal or cellular telephone, and may be configured to receive the notification and responsively display a visible notification and/or emit an audible notification. As another example, remote device 116 may be one or more of the remote sensors described above and may be configured to receive the notification and responsively display a visible notification and/or emit an audible notification, power on, power off, modify one or more parameters, and/or perform one or more tasks. Other remote devices are possible as well.

As shown, robot client 112B is further connected to a call center 118 via a communication link 126. Call center 118 may be any type of system configured to receive the notification. For example, call center 118 may be an emergency call center, a public safety answering point, and/or other service center. Call center 118 may be operated by a user and/or may be automated. To this end, call center 118 may include any type of computing device (e.g., PC, laptop computer, etc.). Other types of call centers are possible as well.

In some embodiments, robot client 112A may be further connected to one or more additional remote devices and/or one or more call centers, such as call center 118 or other call centers. Further, in some embodiments, robot client 112B may be further connected to one or more additional call centers and/or one or more remote devices, such as remote device 116 or other remote devices. In addition, the cloud server 102 may be coupled to the remote device 116 and/or the call center 118, and may be configured to provide the notification.

Any of robot clients 112A and 112B, remote sensors 114A and 114B, remote device 116, and call center 118 may include additional components besides those described above. For example, any of robot clients 112A and 112B, remote sensors 114A and 114B, remote device 116, and call center 118 may include an integrated user-interface (UI) that allows a user to interact with the device. For example, one or both of robot clients 112A and 112B may include various buttons and/or a touchscreen interface that allow a user to provide input. As another example, remote device 116 may include a microphone configured to receive voice commands from a user. Furthermore, any of robot clients 112A and 112B, remote sensors 114A and 114B, remote device 116, and call center 118 may include one or more interfaces that allow various types of user-interface devices to be connected to the client devices.

Each of the communication links 120A, 120B, 122A, 122B, 124, and 126 shown in FIG. 1 may include wired links, such as serial or parallel buses, or wireless links, such as Bluetooth, IEEE 802.11 (IEEE 802.11 may refer to IEEE 802.11-2007, IEEE 802.11n-2009, or any other IEEE 802.11 revision), or other wireless based communication links.

In some examples, the system 100 may include access points through which robot clients 112A and 112B may communicate with the cloud server 102. Access points may take various forms. For example, an access point may take the form of a wireless access point (WAP) or wireless router. As another example, if a robot client 112A or 112B connects using a cellular air-interface protocol, such as a CDMA or GSM protocol, an access point may be a base station in a cellular network that provides Internet connectivity via the cellular network.

As such, robot clients 112A and 112B may include a wired or wireless network interface through which robot clients 112A and 112B can connect to the cloud server 102 (or access points). As an example, robot clients 112A and 112B may be configured to use one or more protocols such as 802.11, 802.16 (WiMAX), LTE, GSM, GPRS, CDMA, EV-DO, and/or HSPDA, among others. Furthermore, robot clients 112A and 112B may be configured to use multiple wired and/or wireless protocols, such as "3G" or "4G" data connectivity using a cellular communication protocol (e.g., CDMA, GSM, or WiMAX, as well as for "WiFi" connectivity using 802.11). Other examples are also possible.

While the remote device 116 and the call center 118 are shown to be coupled directly to the robot clients 112A and 112B, respectively, in some embodiments the remote device 116 and/or the call center 118 may be connected to the robot clients via one or more wires or wireless networks, such as the Internet and/or the cloud server 102. Other examples are possible as well. Further, while robot clients 112A and 112B are shown to be coupled to one another only through the cloud server 102, in some embodiments robot clients 112A and 112B may be directly connected or connectable to one another, as indicated by the communication link 128. Communication link 128 may take the form of any of the wired or wireless links described above.

Figure 2:
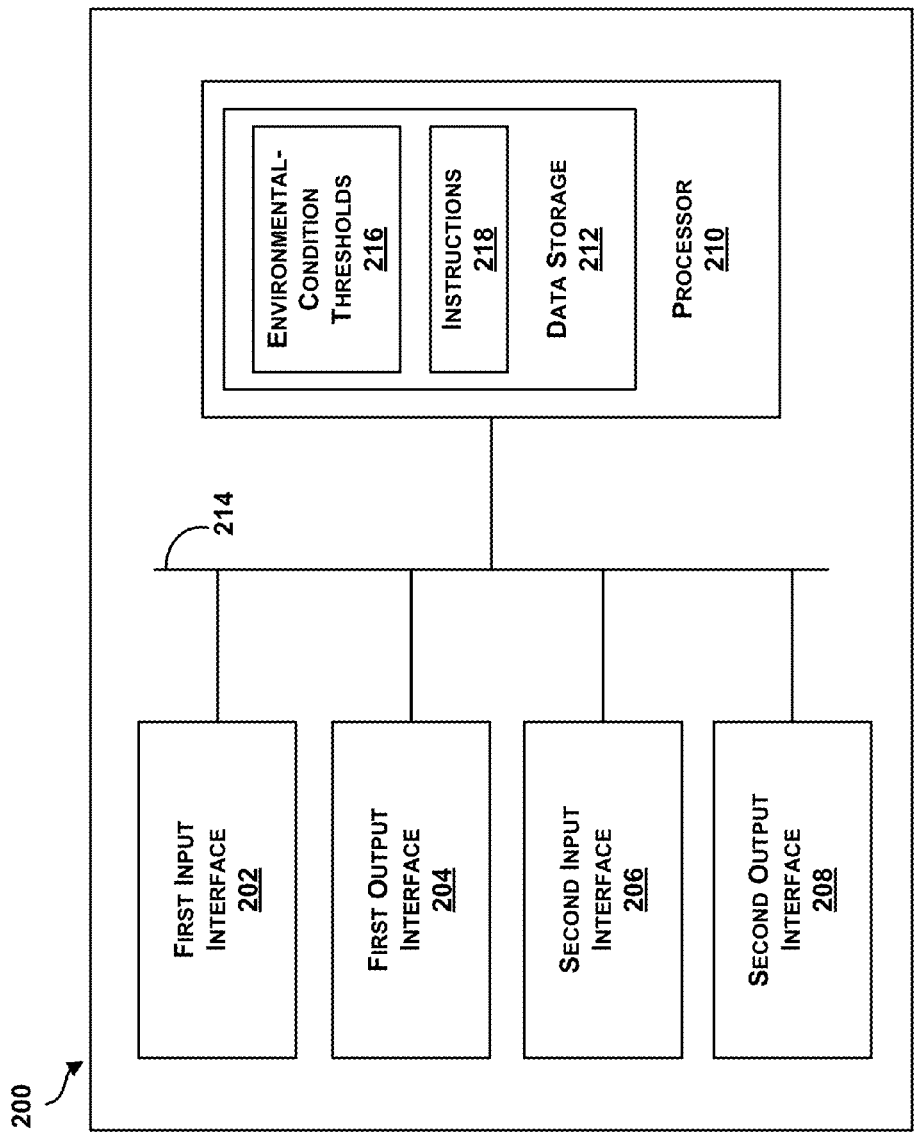
FIG. 2 is a simplified block diagram of an example server.

FIG. 2 is a simplified block diagram of an example server 200. The server 200 may take the form of a cloud server in a cloud-computing architecture, such as the system 100 described above in connection with FIG. 1. As shown, the server 200 includes a first input interface 202, a first output interface 204, a second input interface 206, a second output interface 208, a processor 210, and data storage 212, all of which may be communicatively linked together by a system bus, network, and/or other connection mechanism 214.

The first input interface 202 may be any interface configured to receive from a first robot (such as, for example, robot client 112A, as described above in connection with FIG. 1) first data corresponding to a first environmental condition in a first environment. For example, the first input interface 202 may be a wireless interface. To this end, the first input interface 202 may include an antenna and a chipset for communicating with the first robot over an air interface. The chipset or first input interface 202 in general may be arranged to communicate according to one or more types of wireless communication (e.g. protocols), such as Bluetooth, communication protocols described in IEEE 802.11 (including any IEEE 802.11 revisions), cellular technology (such as GSM, CDMA, UMTS, EV-DO, WiMAX, or LTE), or Zigbee, among other possibilities. Alternately or additionally, the first input interface 202 may be a web-based interface accessible by the first robot. The first input interface 202 may take other forms as well.

The first output interface 204 may be any interface configured to transmit to the first robot instructions to transmit a notification and/or data corresponding to an environmental-condition threshold. To this end, the first output interface 204 may be, for example, a wireless interface, such as any of the wireless interfaces described above.

The second input interface 206 may be any interface configured to receive from a second robot (such as, for example, robot client 112B, as described above in connection with FIG. 1) second data corresponding to the first environmental condition in a second environment. To this end, the second input interface 206 may be, for example, a wireless interface, such as any of the wireless interfaces described above.

The second output interface 208 may be any interface configured to transmit to the second robot instructions to transmit a notification and/or data corresponding to an environmental-condition threshold. To this end, the second output interface 208 may be, for example, a wireless interface, such as any of the wireless interfaces described above.

One or more of the first input interface 202, the first output interface 204, the second input interface 206, and the second output interface 208 may be combined. In some embodiments, the server 200 may include one or more additional interfaces configured to receive data from one or more additional entities, such as other sensors, other robots, and the Internet.

The processor 210 may comprise one or more general-purpose processors and/or one or more special-purpose processors. To the extent the processor 210 includes more than one processor, such processors could work separately or in combination. Further, the processor 210 may be integrated in whole or in part with the first input interface 202, the first output interface 204, the second input interface 206, the second output interface 208, and/or with other components.

Data storage 212, in turn, may comprise one or more volatile and/or one or more non-volatile storage components, such as optical, magnetic, and/or organic storage, and data storage 212 may be integrated in whole or in part with the processor 210. Further, data storage 212 may contain the data received from the first and second robots, as well as other robots and client devices. Additionally, data storage 212 may contain environmental-condition thresholds 216 and instructions 218 (e.g., program logic) executable by the processor 210 to carry out various server functions.

Each environmental-condition threshold 216 may correspond to an environmental condition. For example, environmental-condition thresholds 216 may include a carbon monoxide threshold corresponding to a maximum acceptable level of carbon monoxide in an environment. Other examples are possible as well.

Each environmental-condition threshold 216 may be predetermined based on data corresponding to the environmental condition, such as the data received from the robots and other client devices. Using the example above, the carbon monoxide threshold may be predetermined based on data received from the robots indicating measured levels of carbon monoxide in a number of environments.

In some embodiments, the environmental-condition thresholds 216 may simply be running means or medians of the data received from the robots and other client devices. In other embodiments, the environmental-condition thresholds 216 may be weighted means, quadratic means, truncated means, or other types of means or medians. The environmental-condition thresholds may take other forms as well.

In some embodiments, the environmental-condition thresholds 216 may correspond to more general environmental conditions, such as measured levels of carbon monoxide in environments, or may correspond to more specific environmental conditions, such as measured levels of carbon monoxide in kitchens of residential environments, measured levels of carbon monoxide in commercial environments in the southwest United States, or measured levels of carbon monoxide in July. Other examples are possible as well.

Instructions 218 may be executable by the processor 210 to maintain the environmental-condition thresholds 216. For example, the instructions 218 may be executable by the processor 210 to calculate the running mean or median of the data received from the robots and other client devices corresponding to each environmental condition. Other examples are possible as well.

As noted above, the server 200 may be configured to receive first data corresponding to a first environmental condition via the first input interface 202. Accordingly, the instructions 218 may be further executable by the processor 210 to make a comparison of the first data and an environmental-condition threshold corresponding to the first environmental condition.

Further, the instructions 218 may be executable by the processor 210 to trigger a notification based on the comparison. Triggering the notification may involve, for example, transmitting to the first robot (e.g., via the first output interface 204) instructions to transmit the notification. Alternately, triggering the notification may involve transmitting the notification to another entity, such as a remote device or call center. Triggering the notification may take other forms as well.

Data storage 212 may include additional instructions as well.

Figure 3A:
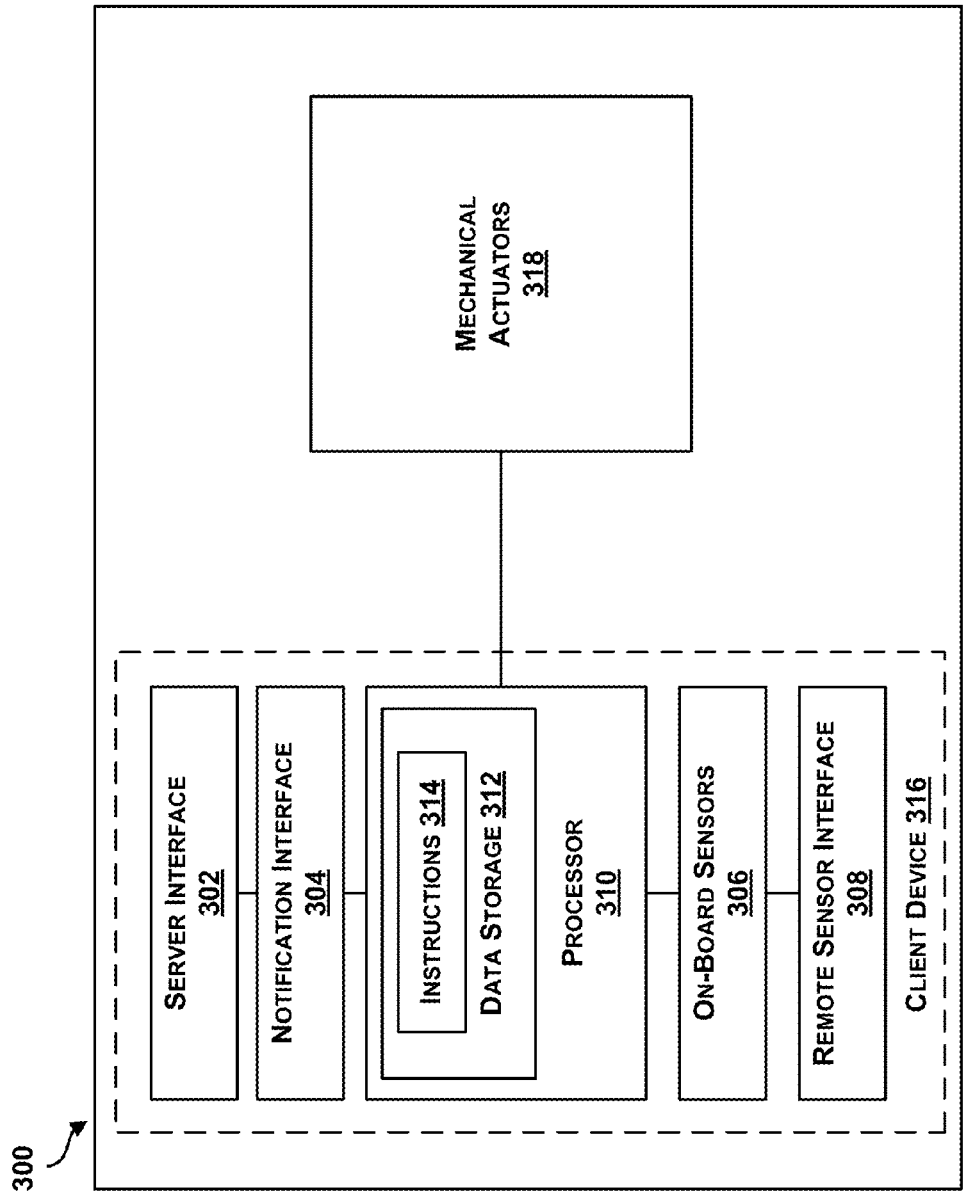
FIG. 3A is a simplified block diagram of an example robot.

FIG. 3A illustrates an example robot 300. The robot 300 may be used as a robot client in a cloud-computing architecture, such as the system 100 described above in connection with FIG. 1. As shown, the robot 300 includes a client device 316 coupled to mechanical actuators 320. The client device 316 may include a server interface 302, a notification interface 304, on-board sensors 306, a remote sensor interface 308, a processor 310, and data storage 312.

The server interface 302 may be any interface configured to transmit data to and receive instructions and/or data from a server, such as the server 200 described above in connection with FIG. 2. The data transmitted to the server may be, for example, data corresponding to an environmental condition in the robot's environment. The instructions received from the server may be, for example, instructions to transmit a notification. The data received from the server may be, for example, an environmental-condition threshold. The server interface 302 may be configured to transmit and receive other information as well.

In some embodiments, the server interface 302 may be a wireless interface. To this end, the server interface 302 may include an antenna and a chipset for communicating with the server over an air interface. The chipset or server interface 302 in general may be arranged to communicate according to one or more types of wireless communication (e.g. protocols), such as Bluetooth, communication protocols described in IEEE 802.11 (including any IEEE 802.11 revisions), cellular technology (such as GSM, CDMA, UMTS, EV-DO, WiMAX, or LTE), or Zigbee, among other possibilities. Alternately or additionally, the server interface 302 may be a web-based application supported by the server and running on the robot client 300. The server interface 302 may take other forms as well.

The notification interface 304 may be any interface configured to transmit a notification. For example, the notification interface 304 may be an interface configured to transmit the notification to a remote device, such as the remote device 116 described above in connection with FIG. 1, or to a call center, such as the call center 118 described above in connection with FIG. 1. To this end, the notification interface 304 may be, for example, a wireless interface, such as any of the wireless interfaces described above.

The on-board sensors 306 may be any sensors configured to collect data corresponding to environmental conditions. On-board sensors 306 may include any of the on-board sensors described above.

The remote sensor interface 308 may be any interface configured to collect data corresponding to environmental conditions from one or more remote sensors. The remote sensors may include any of the remote sensors described above. The remote sensor interface 308 may be, for example, a wireless interface, such as any of the wireless interfaces described above.

The processor 310 may comprise one or more general-purpose processors and/or one or more special-purpose processors. To the extent the processor 310 includes more than one processor, such processors could work separately or in combination. Further, the processor 310 may be integrated in whole or in part with the server interface 302, the notification interface 304, any of the on-board sensors 306, the remote sensor interface 308, and/or with other components.

Data storage 312, in turn, may comprise one or more volatile and/or one or more non-volatile storage components, such as optical, magnetic, and/or organic storage, and data storage 312 may be integrated in whole or in part with the processor 310. Further, data storage 312 may contain instructions 314 (e.g., program logic) executable by the processor 310 to carry out various robot functions.

For example, the instructions 314 may be executable by the processor 310 to control the on-board sensors 306 to collect data and, in some cases, to analyze the data. The instructions 314 may be further executable by the processor 310 to control the remote sensor interface 308 to receive the data collected by the remote sensors and, in some cases, to analyze the data. The data collected through the on-board sensors 306 and/or the remote sensor interface 308 may be data corresponding to an environmental condition in an environment of the robot 300.

Further, the instructions 314 may be executable by the processor 310 to transmit the data collected through the on-board sensors 306 and/or the remote sensor interface 308 to the server via the server interface 302, and to receive the instructions to transmit a notification from the server via the server interface 302. Alternately or additionally, the instructions 314 may be executable by the processor 310 to transmit to the server a request for an environmental-condition threshold corresponding to the environmental condition, and to receive the environmental-condition threshold. Further, the instructions 314 may be further executable by the processor 310 to make a comparison of the data collected through the on-board sensors 306 and/or the remote sensor interface 308 with the environmental-condition threshold and, based on the comparison, decide to transmit a notification.

Further, the instructions 314 may be executable by the processor 310 to transmit the notification. The instructions 314 may be executable by the processor 310 to perform other robot functions as well.

In some embodiments, the client device 316 may be a module that can be connected to and disconnected from the robot 300. For example, the client device 316 may be a mobile device or tablet computer. Other examples are possible as well.

In some embodiments, the client device 316 may be configured to physically connect to the robot 300, such as by sitting on a "chest" of the robot 300 to form an interactive display. In other embodiments, the client device 316 may be configured to wirelessly connect to the robot 300 through, for example, a Bluetooth connection. Other wireless technologies are possible as well.

In some embodiments, the client device 316 may include one or more sensors that, when the client device 316 is connected to the robot 300, serve as the on-board sensors 308 for the robot 300. For example, in embodiments where the client device 316 comprises a tablet computer, the sensors may include those often found in tablet computers such as, for example, GPS receivers and cameras. Other examples are possible as well.

In some embodiments, the client device 316 may be configured to interact with the server whether connected to the robot 300 or not, and may share information with the robot 300 when connected. This may allow a user to download new routines for the robot 300 from the cloud. For example, a laundry folding routine may be stored on the cloud, and a user may be able to select this routine using the client device 316 to download the routine from the cloud, and when the client device 316 is placed into or coupled to the robot 300, the robot 300 would be able to perform the downloaded action. Other examples are possible as well.

In some embodiments, one or more of the server interface 302, the notification interface 304, the on-board sensors 306, the remote sensor interface 308, the processor 310, and the data storage 312 may be modules that can be removably connected to the client device 316 and/or the robot 300. For example, one or more on-board sensors may be removably connected to the client device 316 and/or the robot 300. This may allow a user to configure the types of data that will be collected by the robot 300. For example, a user may connect an ambient temperature sensor to the client device 316 and/or the robot 300, and the robot 300 may then be able to collect data corresponding to the ambient temperature in an environment. Further, this may allow the robot 300 to vary power consumption based on, for example, a battery power level of the robot 300. For example, the robot 300 may power off one or more on-board sensors to conserve power. Other examples are possible as well.

In embodiments where one or more of the client device 316, the server interface 302, the notification interface 304, the on-board sensors 306, the remote sensor interface 308, the processor 310, and the data storage 312 are modules, any of the modules may be interconnected, and/or may communicate to receive data or instructions from each other so as to provide a specific output or functionality for the robot 300.

The mechanical actuators 318 may include a moveable base, motors, wheels, movable arms, and/or other elements that enable robot 300 to move in or interact with the environment.

Figure 3C:
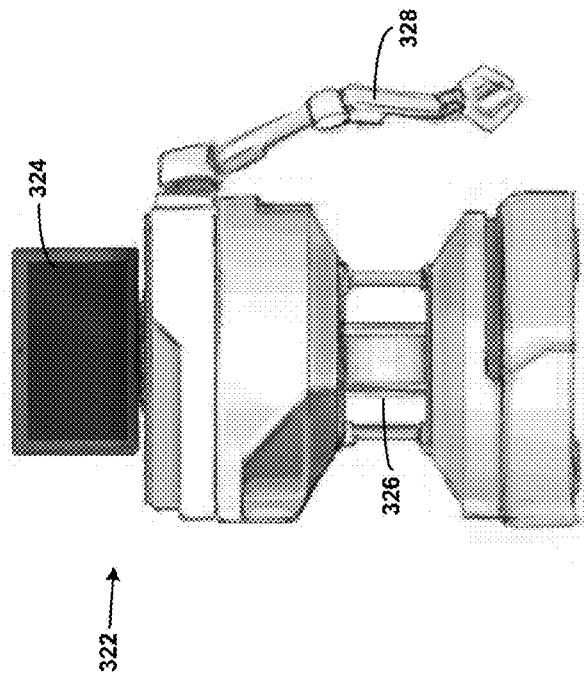
FIG. 3C illustrates another graphical example of a robot.
Figure 3B:
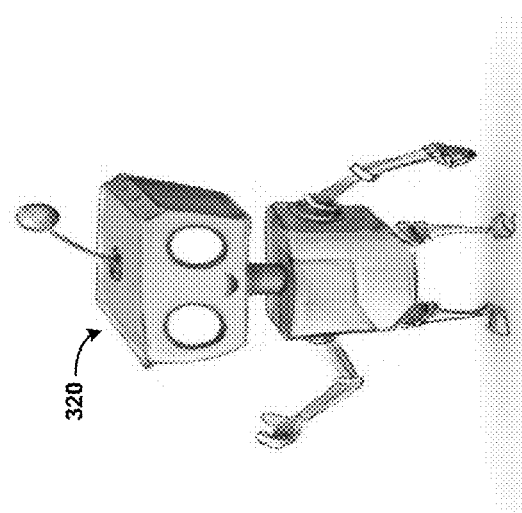
FIG. 3B illustrates a graphical example of a robot.

FIG. 3B illustrates a graphical example of a robot 320. In FIG. 3B, the robot 320 is shown as a mechanical form of a person including arms, legs, and a head. The robot 320 may be configured to receive any number of client devices or modules, as described above. In some embodiments, the robot 320 may be configured to receive a client device that is configured to operate the robot 320.

FIG. 3C illustrates another example of a robot 322. The robot 322 includes a client device 324, sensors 326, and a mechanical actuator 328. In this example, the client device 324 may be a mobile device or a tablet computer. Other examples are possible as well. In some embodiments, the client device 324 may include or may be connectable to the sensors 326. The sensors 326 may include any of the on-board sensors described above. The mechanical actuator 328 may include a base, wheels, and a motor. In some embodiments, such as that shown, client device 324 and the sensors 326 can be positioned on the mechanical actuator 328. The robot 322 may be configured in other ways as well.

Any of the robots illustrated in FIGS. 3A-3C may be configured to operate according to a robot operating system (e.g., an operating system designed for specific functions of the robot). A robot operating system may provide libraries and tools (e.g., hardware abstraction, device drivers, visualizers, message-passing, package management, etc.) to enable robot applications. Examples of robot operating systems include open source software such as ROS (robot operating system), DROS, or ARCOS (advanced robotics control operating system), proprietary software, and other examples. A robot operating system may include publish and subscribe functionality, and may also include functionality to control components of the robot, such as head tracking, base movement (e.g., velocity control, navigation framework), etc.

Figure 4A:
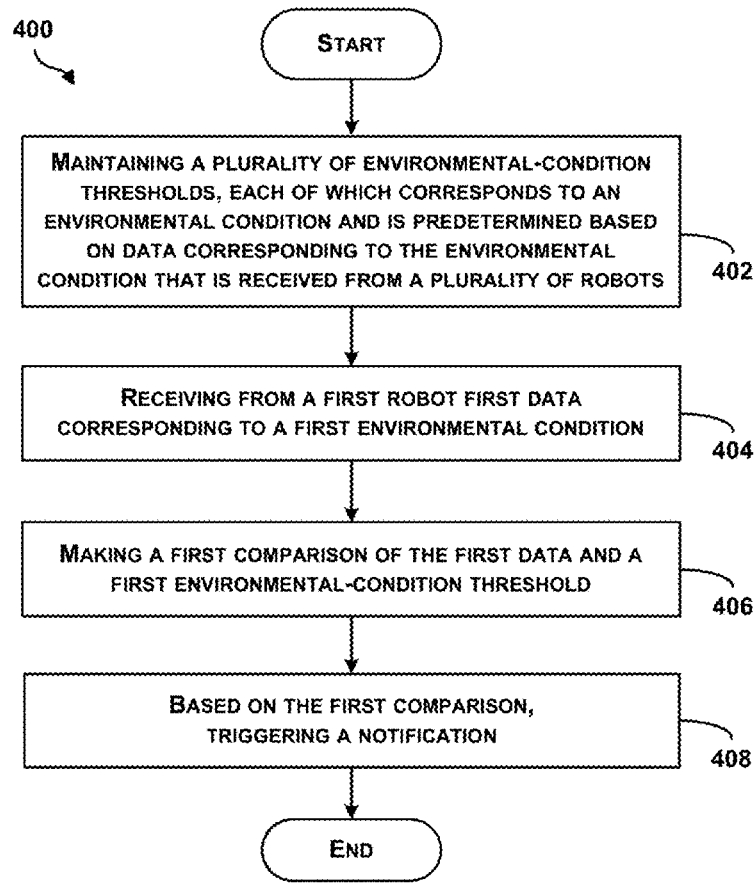
FIG. 4A is a block diagram of an example method of a first robot interacting with the cloud to monitor an environmental condition in a first environment.

FIG. 4A is a block diagram of an example method of a first robot interacting with the cloud to monitor an environmental condition in a first environment.

Method 400 shown in FIG. 4A presents an embodiment of a method that, for example, could be used with systems, devices, and servers described herein. Method 400 may include one or more operations, functions, or actions as illustrated by one or more of blocks 402-408. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 400 and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include a non-transitory computer readable medium, for example, such as computer-readable media that store data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example.

In addition, for the method 400 and other processes and methods disclosed herein, each block may represent circuitry that is wired to perform the specific logical functions in the process.

As shown, the method 400 begins at block 402 where a server maintains a plurality of environmental-condition thresholds, each of which corresponds to an environmental condition and is predetermined based on data corresponding to the environmental condition that is received from a plurality of robots. To this end, the server may store the data corresponding to each environmental condition in data storage, and may determine (e.g., periodically, or on an as-needed basis) the environmental-condition threshold corresponding to the environmental condition using the data received from the robots. For example, each environmental-condition threshold may comprise a running mean of the data corresponding to the environmental condition that is received from the robots. The environmental-condition thresholds may take other forms as well.

The method 400 continues at block 404 where the server receives from a first robot first data corresponding to a first environmental condition. The first robot may be one of the plurality of robots from which the server receives data. The first data may include or may be derived from data collected at the first robot via, for example, one or more on-board or remote sensors. In some embodiments, the first data may include the data corresponding to the first environmental condition as well as an indication of the first environmental condition. Alternately or additionally, the first data may include an indication of a first environment in which the first robot is located. The first data may take other forms as well.

The method 400 continues at block 406 where the server makes a first comparison of the first data and a first environmental-condition threshold in the plurality of environmental-condition thresholds maintained at the server. Depending on the environmental condition, the environmental-condition threshold may be a maximum or a minimum. For example, a carbon monoxide threshold may correspond to a maximum acceptable level of carbon monoxide in an environment. On the other hand, a temperature threshold may correspond to a minimum acceptable temperature in an environment. Generally, the first comparison may indicate whether the first environmental condition is at an acceptable level or an unacceptable level in the first environment.

The method 400 continues at block 408 where, based on the first comparison, the server triggers a notification. For example, if the first comparison indicates that the first environmental condition is at an unacceptable level, the server may trigger the notification, while if the first comparison indicates that the first environmental condition is at an acceptable level, the server may not trigger the notification. In some embodiments, the server may only trigger the notification if the first environmental condition is at an unacceptable level for a certain amount of time. In one instance, the first environmental-condition threshold may be a threshold range. An acceptable level may therefore be a level that is within the threshold range, while an unacceptable level may be a level that is outside of the threshold range. Other examples are also possible, and the example of a threshold range is not meant to be limiting.

The notification may take several forms, depending on the recipient. For example, the notification may be a Short Message Service (SMS) or Multimedia Message Service (MMS) message, a telephone call (e.g., a prerecorded message), or an email. Further, the notification message may include instructions to display a visual notification (e.g., an SMS or MMS message, an email, a visual alarm, or a light), to emit an audible notification (e.g., a prerecorded message or an alarm), to power on, to power off, to modify one or more parameters, and/or to perform one or more tasks. The notification may take other forms as well.

Triggering the notification may involve the server causing the first robot to transmit the notification. To this end, the server may transmit to the first robot instructions to transmit the notification. The instructions may include, for example, an indication of the first environmental condition, and indication of the unacceptable level, and/or an indication of one or more entities to which the notification should be transmitted. Alternately or additionally, triggering the notification may involve the server directly transmitting the notification to the one or more entities. Example entities include a laptop, mobile telephone, smartphone, personal digital assistant, tablet, personal or cellular telephone, one or more of the remote sensors, and a call center, such as an emergency call center, a public safety answering point, and/or other service center. Other entities are possible as well.

In some embodiments, triggering the notification may involve making a determination whether the notification comprises an emergency notification. When the notification comprises an emergency notification, the server and/or robot may transmit the notification to both the emergency call center and the remote device(s), while when the notification does not comprise an emergency notification, the server may transmit the notification only to the remote device(s).

Figure 4B:
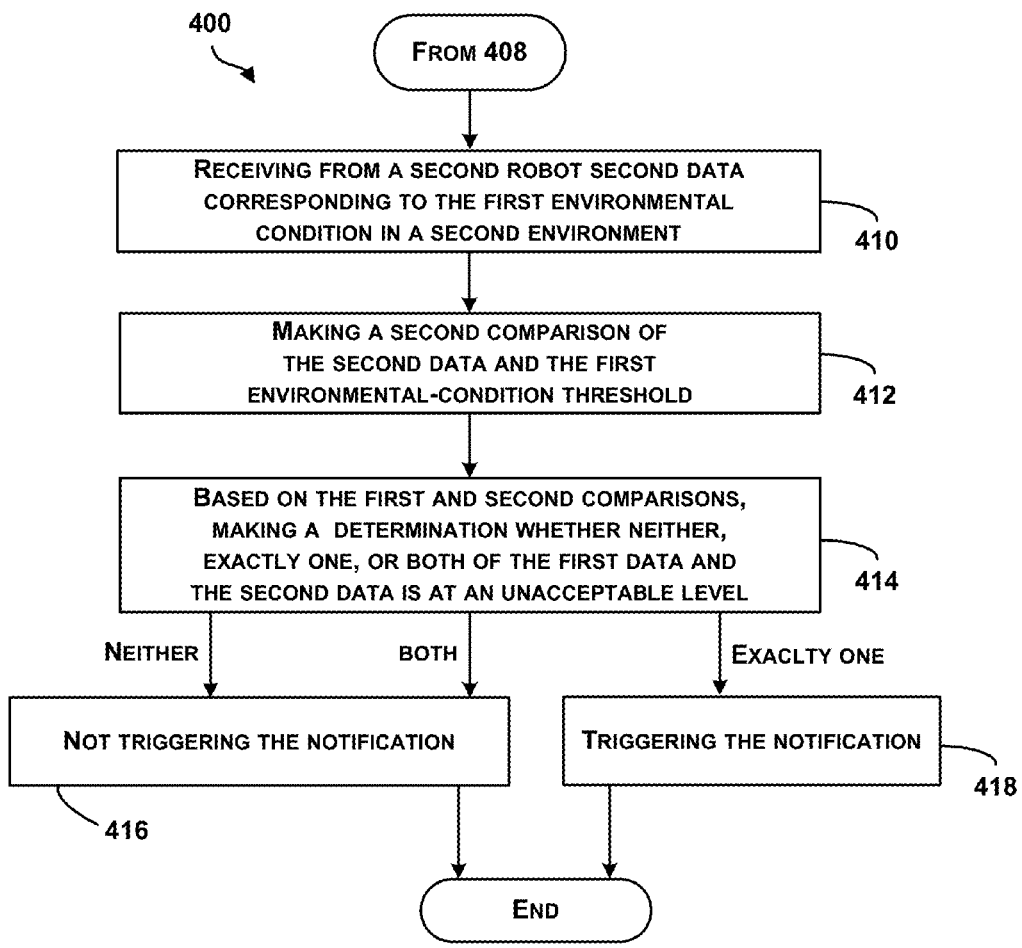
FIG. 4B is a block diagram of an example method of a second robot interacting with the cloud to monitor the environmental condition in a second environment.

In some embodiments, the method 400 may further include the server receiving data from a second robot. FIG. 4B is a block diagram of an example method of a second robot interacting with the cloud to monitor the environmental condition in a second environment. As shown, the method 400 may continue at block 410 where the server receives from a second robot second data corresponding to the first environmental condition in a second environment. The second environment may be co-located with the first environment, or may be remote from the first environment. For example, the first environment may be a first home, and the second environment may be a second home next door to the first home. Other examples are possible as well.

The method 400 may continue at block 412 where the server makes a second comparison of the second data and the first environmental-condition threshold. Similar to the first comparison, the second comparison may generally indicate whether the first environmental condition is at an acceptable level or an unacceptable level in the second environment.

The method 400 may continue at block 414 where, based on the first and second comparisons, the server makes a third determination whether neither, exactly one, or both of the first data and the second data is at an unacceptable level.

Responsive to a determination that neither of the first data and the second data is at an unacceptable level, the server may not trigger a notification at block 416. Further, responsive to a determination that both of the first data and the second data is at an unacceptable level, the server may also not trigger a notification at block 416. Still further, responsive to a determination that exactly one of the first data and the second data is at an unacceptable level, the server may trigger a notification at block 418. This may prevent the robot from triggering a notification based on an event outside the robot's environment.

For example, the first environmental condition may be a noise level. When neither of the first data and the second data indicates that the noise level in the first and second environments, respectively, is at unacceptable level, there may be no need for the server to trigger a notification. Similarly, when both of the first data and the second data indicate that the noise level in the first and second environments, respectively, are at unacceptable level, there may be no need for the server to trigger a notification. This is because if the noise levels in both the first and the second environments are unacceptable, the source of the noise may not be local to either of the first and second environments. In the example where the first and second environments are neighboring houses, for instance, the source of the noise may be in the street, such that there is no need to trigger a notification from either of the first and second environments. On the other hand, when exactly one of the first data and the second data indicates that the noise level in exactly one of the first and second environments is at an unacceptable level, there may be a need for the server to trigger a notification. This is because if the noise level is only unacceptable in exactly one of the first and second environments, the source of noise is likely local to the exactly one environment.

Figure 5:
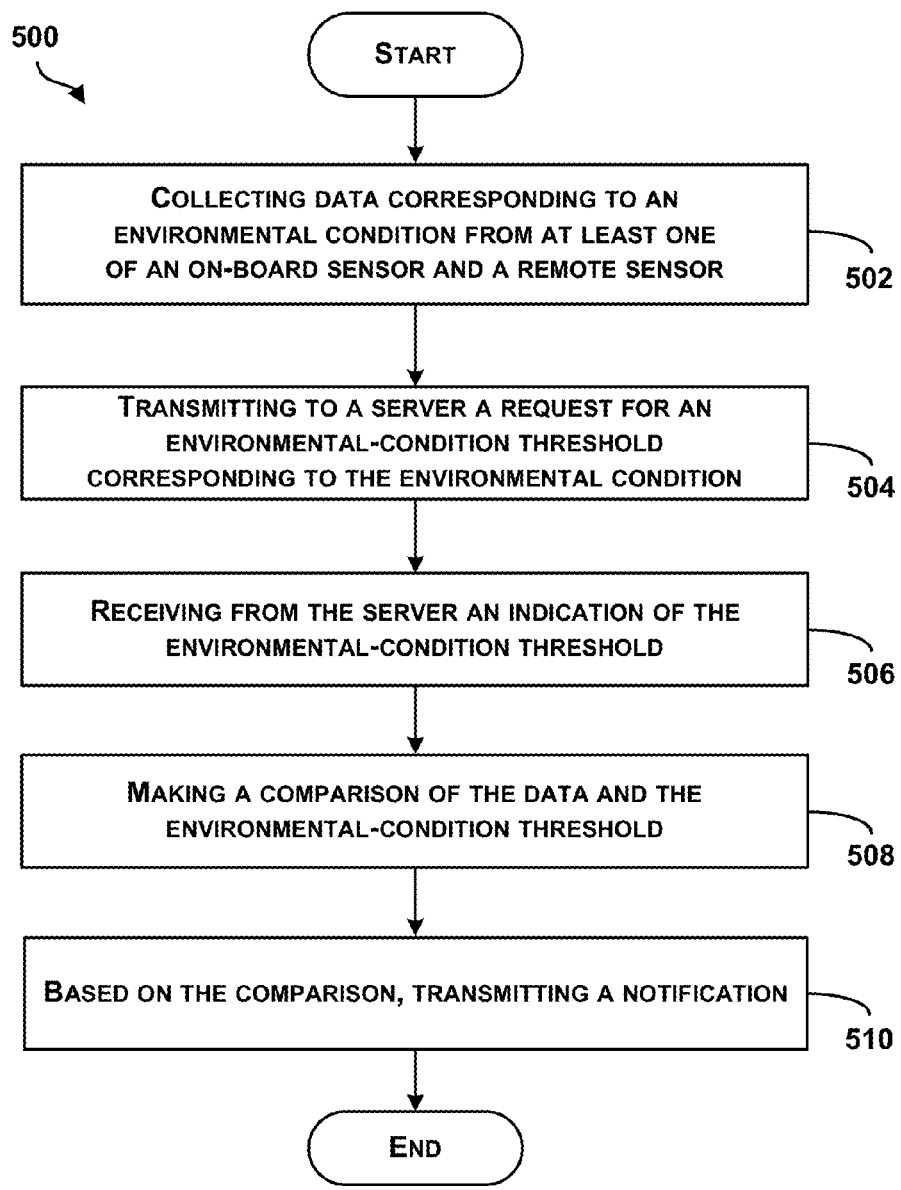
FIG. 5 is a block diagram of another example method of a robot interacting with the cloud to monitor an environmental condition in an environment, all arranged in accordance with at least some embodiments described herein.

In some embodiments, the comparison of data collected at a robot and an environmental-threshold, as described above at block 406, may be carried out by the robot, rather than at the server. FIG. 5 is a block diagram of another example method of a robot interacting with the cloud to monitor an environmental condition in an environment.

The method 500 begins at block 502 where a robot collects data corresponding to an environmental condition from at least one of an on-board sensor and a remote sensor. The on-board and remote sensors may take any of the forms described above.

At block 504, the robot transmits to a server a request for an environmental-condition threshold corresponding to the environmental condition. To this end, the robot may transmit to the server one or more of an indication of the environmental condition, an indication of the robot, and an indication of the robot's environment. The robot may transmit to the server other information as well.

At block 506, the robot receives from the server an indication of the environmental-condition threshold. At block 508, the robot makes a comparison of the data and the environmental-condition threshold. The comparison may generally indicate whether the environmental condition is at an acceptable or an unacceptable level.

At block 510, the robot may, based on the comparison, transmit a notification. For example, if the comparison indicates that the environmental condition is at an unacceptable level, the robot may trigger the notification, while if the comparison indicates that the environmental condition is at an acceptable level, the robot may not trigger the notification. In some embodiments, the robot may only trigger the notification if the environmental condition is at an unacceptable level for a certain amount of time.

Triggering the notification may involve the robot transmitting the notification to the one or more entities, such as any of the entities described above.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
maintaining, by a cloud server, an environmental-condition threshold that corresponds to an environmental condition and is determined based on data corresponding to the environmental condition that is received via a network interface of the cloud server from a plurality of robots, wherein the received data is indicative of measured levels of the environmental condition in respective environments of the plurality of robots;
receiving, via the network interface and from a first robot, first data corresponding to the environmental condition in a first environment of the first robot;
making, by the cloud server, a first comparison of the first data and the environmental-condition threshold; and
based on the first comparison, triggering a notification.

2. The method of claim 1, wherein the environmental-condition threshold comprises a running mean of the data corresponding to the environmental condition and received from the plurality of robots.

3. The method of claim 1, wherein triggering the notification comprises causing the first robot to transmit the notification.

4. The method of claim 1, further comprising transmitting the notification to at least one of an emergency call center and a remote device.

5. The method of claim 1, further comprising:
receiving from a second robot second data corresponding to the environmental condition in a second environment; and
making a second comparison of the second data and the environmental-condition threshold,
wherein triggering the notification further comprises triggering the notification based on the first comparison and the second comparison.

6. The method of claim 1, wherein triggering the notification based on the first comparison comprises triggering the notification based on the first comparison being indicative that the environmental condition is at an unacceptable level.

7. A cloud server, comprising:
a network interface;
at least one processor; and
data storage comprising instructions executable by the at least one processor to:
maintain an environmental-condition threshold that corresponds to an environmental condition and is determined based on data corresponding to the environmental condition that is received via the network interface from a plurality of robots, wherein the received data is indicative of measured levels of the environmental condition in environments of the plurality of robots;

receive from a first robot first data corresponding to the environmental condition in a first environment of the first robot;

make a first comparison of the first data and the environmental-condition threshold; and based on the first comparison, trigger a notification.

8. The cloud server of claim 7, wherein the environmental-condition threshold comprises a running mean of the data corresponding to the environmental condition and received from the plurality of robots.

9. The cloud server of claim 7, wherein triggering the notification comprises causing the first robot to transmit the notification.

10. The cloud server of claim 7, further comprising instructions executable by the at least one processor to transmit the notification to at least one of an emergency call center and a remote device.

11. The cloud server of claim 7, further comprising instructions executable by the at least one processor to:

receive from a second robot second data corresponding to the environmental condition in a second environment; and make a second comparison of the second data and the environmental-condition threshold, wherein triggering the notification further comprises triggering the notification based on the first comparison and the second comparison.

12. A method comprising:

receiving, via a network interface of a robot and from a cloud server, an indication of an environmental-condition threshold that corresponds to an environmental condition and is determined based on data corresponding to the environmental condition that is received by the cloud server from a plurality of robots, wherein the received data is indicative of measured levels of the environmental condition in environments of the plurality of robots;

obtaining, by the robot, first data corresponding to the environmental condition in a first environment of the robot;

making, by the robot, a first comparison of the first data and the environmental-condition threshold; and based on the first comparison, triggering a notification.

13. The method of claim 12, further comprising transmitting to the cloud server a request for the environmental-condition threshold.

14. The method of claim 12, wherein obtaining the first data corresponding to the environmental condition in the first environment of the robot comprises collecting first data corresponding to the environmental condition in the first environment using at least one on-board sensor of the robot.

15. The method of claim 14, wherein the at least one on-board sensor is selected from the group consisting of: a gyroscope, an accelerometer, a compass, a Global Positioning System (GPS) receiver, a light sensor, an infrared sensor, an optical sensor, a biosensor, a radio sensor, a Radio Frequency identification (RFID) system, a wireless sensor, a camera, a light sensor, a motion sensor, a range sensor, a microphone or other audio sensor, a speaker, a radar, a capacitive sensor, a touch sensor, a smoke sensor, a carbon monoxide sensor, a natural gas sensor, a pyro sensor, a heat sensor, a water sensor, and a biometric sensor.

16. The method of claim 12, wherein obtaining the first data corresponding to the environmental condition in the first environment of the robot comprises obtaining first data corresponding to the environmental in the first environment using at least one remote sensor interface coupled to at least one remote sensor.

17. The method of claim 16, wherein the at least one remote sensor is selected form the group consisting of: a light sensor, an infrared sensor, an optical sensor, a biosensor, a radio sensor, a Radio Frequency identification (RFID) system, a wireless sensor, a camera, a light sensor, a motion sensor, a range sensor, a microphone or other audio sensor, a speaker, a radar, a capacitive sensor, a touch sensor, a smoke sensor, a carbon monoxide sensor, a natural gas sensor, a pyro sensor, a heat sensor, a water sensor, a biometric sensor, an appliance, a washing machine, a dryer, a refrigerator, an oven, a stove, a toaster, a coffee maker, a furnace, an air conditioning unit, a heating unit, a television, a computer, a fire alarm, and a security system.

18. The method of claim 16, further comprising verifying the first data using at least one on-board sensor of the robotic device prior to transmitting the notification.

19. The method of claim 12, further comprising transmitting the notification to at least one of an emergency call center and a remote device.

20. The method of claim 12, wherein triggering the notification based on the first comparison comprises triggering the notification based on the first comparison being indicative that the environmental condition is at an unacceptable level.

* * * * *